United States Patent
Wu et al.

(10) Patent No.: US 7,460,974 B2
(45) Date of Patent: Dec. 2, 2008

(54) MULTIPLE-POINT SMOOTHING METHOD FOR MOTOR-SPEED ESTIMATION

(75) Inventors: Jia-Ming Wu, Taoyuan Shien (TW);
Po-Ming Chen, Taoyuan Shien (TW);
Dong-Hai Wang, Taoyuan Shien (TW)

(73) Assignee: Delta Electronics, Inc., Taoyuan Hsien (TW)

(*) Notice: Subject to any disclaimer, the term of this patent is extended or adjusted under 35 U.S.C. 154(b) by 0 days.

(21) Appl. No.: 11/772,890

(22) Filed: Jul. 3, 2007

(65) Prior Publication Data

US 2008/0021670 A1      Jan. 24, 2008

(51) Int. Cl.
*G01P 3/00* (2006.01)

(52) U.S. Cl. .............. 702/142; 702/145; 702/146; 324/160; 324/173; 318/568.17; 318/568.22

(58) Field of Classification Search ............... 702/142, 702/145, 146; 324/173, 160; 318/592, 568.17, 318/568.22, 632
See application file for complete search history.

(56) References Cited

U.S. PATENT DOCUMENTS

| | | | |
|---|---|---|---|
| 5,886,491 A * | 3/1999 | Yoshida et al. ............. | 318/592 |
| 2007/0043528 A1 | 2/2007 | Bae | |

* cited by examiner

*Primary Examiner*—Tung S Lau
*Assistant Examiner*—Hien X Vo

(57) ABSTRACT

A multiple-point smoothing method for motor-speed estimation. The output of an encoder is over-sampled to obtain over-sampled position differences according to an over-sampling factor M. The over-sampled position differences are averaged to obtain an initial speed estimation. The initial speed estimation is low-pass filtered to obtain a final speed estimation. The final speed estimation is sent to a speed controller to control the speed of a motor. Alternatively, in a composite multiple-point smoothing scheme, the initial speed estimations based on two over-sampling factors are obtained. One of the initial speed estimations is selected based on an average of the two estimations, and the selected initial speed estimation is further processed to obtain a final speed estimation. The method of the present invention can reduce ripple in estimated speed of motor when the motor is operated at high speed.

7 Claims, 8 Drawing Sheets

MULTIPLE-POINT SMOOTHING METHOD FOR MOTOR-SPEED ESTIMATION

BACKGROUND OF THE INVENTION

1. Field of the Invention

The present invention relates to a method for motor-speed estimation, especially to a multiple-point smoothing method for motor-speed estimation.

2. Description of Prior Art

Speed measurement is inevitable for close loop control of motor. For speed measurement of motor, an encoder is used to measure the rotational speed of motor rotor. It is difficult to measure the speed of rotor with smooth and real-time property because the encoder generally does not have sufficient resolution for position quantization. However, smooth and real-time requirement is essential to automatic control. A smooth speed measurement can suppress running noise and vibration of machine. A real-time speed measurement provides fidelity for genuine speed of motor and has reduced delay to enhance high speed operation.

FIG. 1 shows the block diagram of a prior art motor controlling system, which controls the speed of a motor $10a$ based on a feedback measured speed of motor. A speed estimation device $20a$ comprises a counter $22a$ and a speed estimation unit $24a$. An encoder $12a$ outputs a pulse signal to represent a measured motor position. The counter $22a$ processes the pulse signal to obtain a position signal P for the motor. The speed estimation unit $24a$ processes the position signal P of the motor to obtain a motor rotational speed $V_{LPF}$. A position control unit $40a$ generates a speed command $V_{cmd}$ based on a position command $P_{cmd}$ and a feedback from the counter $22a$. A speed control unit $30a$ generates a current command $i_{cmd}$ based on the speed command $V_{cmd}$ and sends the current command $i_{cmd}$ to a current controlling and driving unit $50a$. The current controlling and driving unit $50a$ accordingly drives the motor $10a$ based on the current command $i_{cmd}$.

With reference to FIGS. 2 and 3, the processing principle and processing steps for the prior art speed estimation unit $24a$ are illustrated. As shown in FIG. 2, the prior art speed estimation unit $24a$ uses a displacement within a unit time to calculate the speed V(t) of the motor.

$$V(t) = \frac{P(t) - P(t-T)}{T},$$

wherein V(t) is an estimated speed, P(t) is a feedback counted position of the encoder and T is sampling time. As shown in FIG. 3, at each sampling time T (step S$10a$), the speed estimation unit $24a$ reads a counted position P(t) from the counter (step S$12a$). The speed estimation unit $24a$ then subtracts the position P(t−T) of previous sample from the current position P(t) (step S$14a$). The speed estimation unit $24a$ divides the position difference by the sampling time T to obtain an initial speed $$V(t) = \frac{P(t) - P(t-T)}{T}$$

(step S$16a$). The initial speed is processed by a low pass filter for smoothing treatment to obtain a final speed estimation $V_{LPF}$ (step S$18a$).

The speed estimation in prior art speed estimation unit $24a$ has ripple problem due to the position quantization error of encoder. Provided that the encoder can generate $N_t$ pulse per turn and the sampling frequency is fs Hz. The ripple speeds fr, namely the estimated speed at which ripple occurs, are multiple of $(60*fs/N_t)$ rpm.

In motor rotation speed measurement, provided that the sampling time is $(6\ kHz)^{-1}$ and the resolution per turn is 10000 pulses/turn, the ripple speed fr is the multiple of 36 rpm, when the motor speed increases from 0 rpm to 500 rpm. It means that the motor controller has ripple at those motor speeds.

US patent publication 20070043528 A1 discloses a method for averaging speed estimations based on multiple sampling periods to reduce ripple, where a moving average window is used. However, this prior art method cannot solve the phase delay problem when the motor is operated at high speed.

SUMMARY OF THE INVENTION

It is an object of the present invention to provide a method for motor-speed estimation with smooth property for high speed motor.

Accordingly, the present invention provides a multiple-point smoothing method for motor-speed estimation. The output of an encoder is over-sampled to obtain over-sampled position differences according to an over-sampling factor M. The over-sampled position differences are averaged to obtain an initial speed estimation. The initial speed estimation is low-pass filtered to obtain a final speed estimation. The final speed estimation is sent to a speed controller to control the speed of a motor.

Alternatively, in a composite multiple-point smoothing scheme, the initial speed estimations based on two over-sampling factors are obtained. One of the initial speed estimations is selected based on an average of the two estimations, and the selected initial speed estimation is further processed to obtain a final speed estimation. The method of the present invention can reduce ripple in estimated speed of motor when the motor is operated at high speed.

BRIEF DESCRIPTION OF DRAWING

The features of the invention believed to be novel are set forth with particularity in the appended claims. The invention itself however may be best understood by reference to the following detailed description of the invention, which describes certain exemplary embodiments of the invention, taken in conjunction with the accompanying drawings in which:

DETAILED DESCRIPTION OF THE INVENTION

Figure 1:
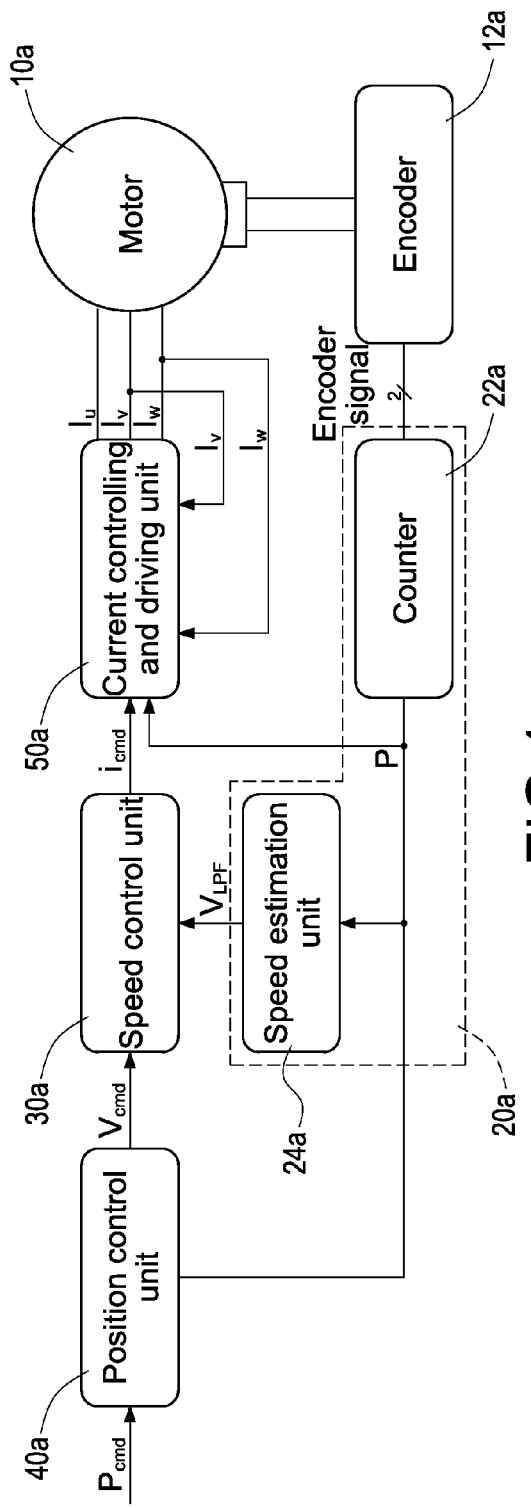
FIG. 1 shows the block diagram of a prior art motor controlling system.
Figure 2:
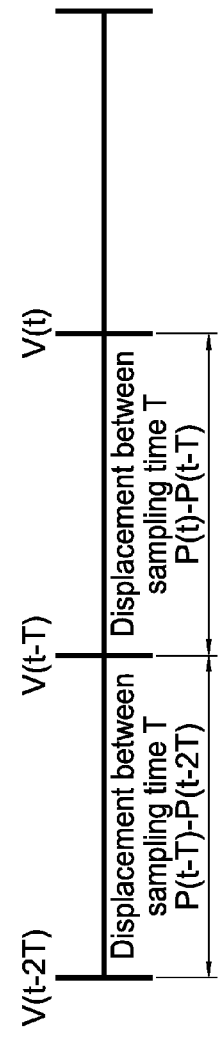
FIG. 2 shows processing principle for the prior art speed estimation unit.
Figure 3:
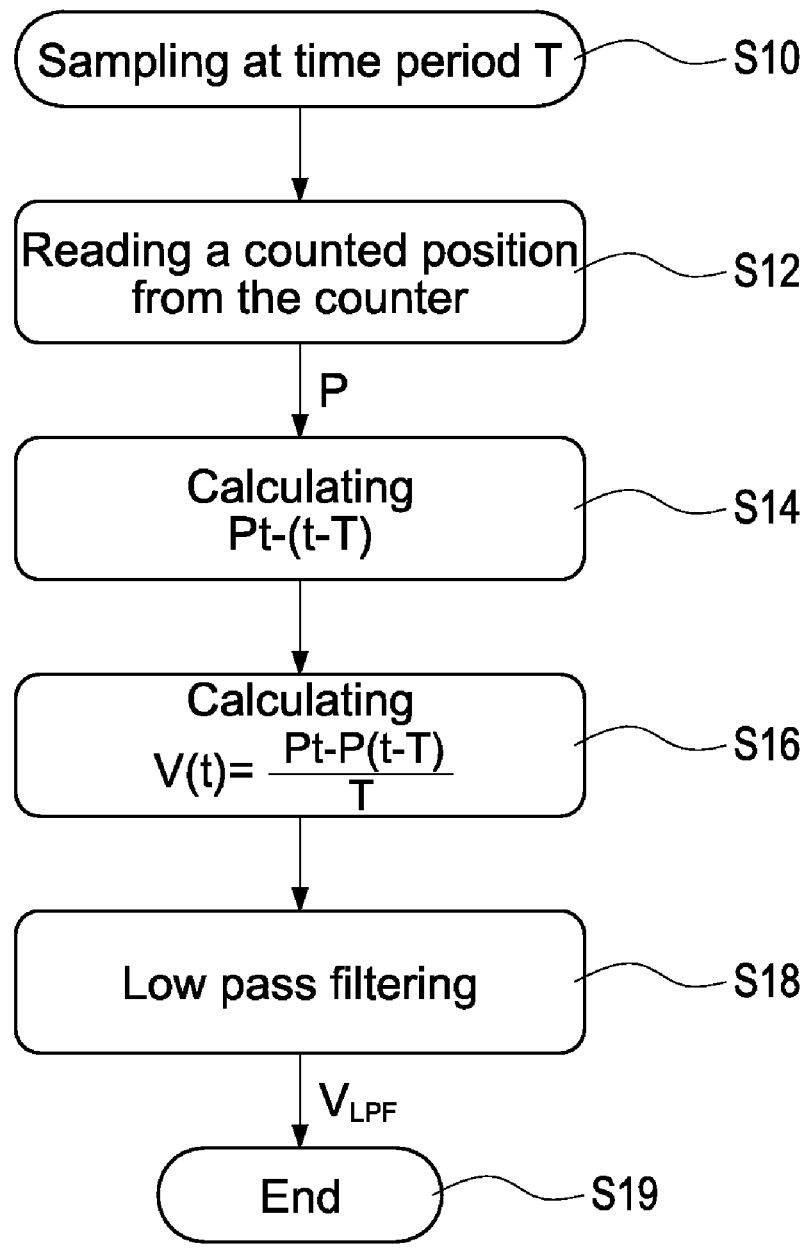
FIG. 3 shows processing steps for the prior art speed estimation unit.
Figure 4:
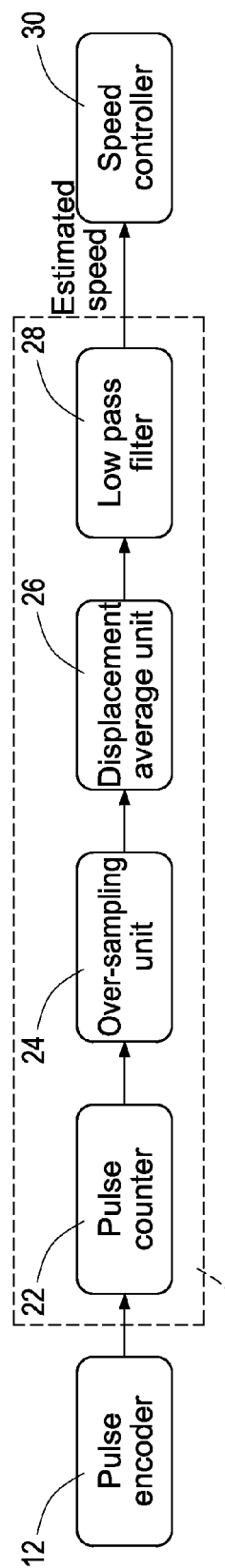
FIG. 4 shows a block diagram of a speed estimation apparatus for realizing the multiple-point smoothing method according to the present invention.

FIG. 4 shows a block diagram of a speed estimation apparatus 20 for realizing the multiple-point smoothing method according to the present invention. The speed estimation apparatus 20 is connected between a pulse encoder 12 and a speed controller 30. The speed estimation apparatus 20 reads a position information of motor from the pulse encoder 12 to provide a speed estimation for motor. The speed estimation is sent to the speed controller 30 for feedback controlling a motor (not shown).

The speed estimation apparatus 20 according to the present invention comprises a pulse counter 22, an over-sampling unit 24, a displacement average unit 26 and a low pass filter 28.

The pulse counter 22 counts output pulses from the encoder and can be implemented by a conventional counter. The over-sampling unit 24 samples the counted pulses with discrete time points. The sampling frequency of the over-sampling unit 24 is M times of a rated sampling frequency for the counter. Provided that the rated sampling frequency is fs Hz and therefore the sampling period is T=1/fs (Sec), the over-sampling unit 24 has an over sampling frequency of M*fs Hz and the over sampling time is Ts=1/(M*fs) Sec, wherein M is an over sampling factor and preferably an integer larger than one. The displacement average unit 26 averages M sets of displacements and then divides the averaged displacements by period T to obtain an initial speed estimation V(t). The low pass filter 28 performs a low pass filtering to the initial speed estimation V(t) to obtain a final speed estimation. The final speed estimation can be used for close loop control of motor.

Figure 5:
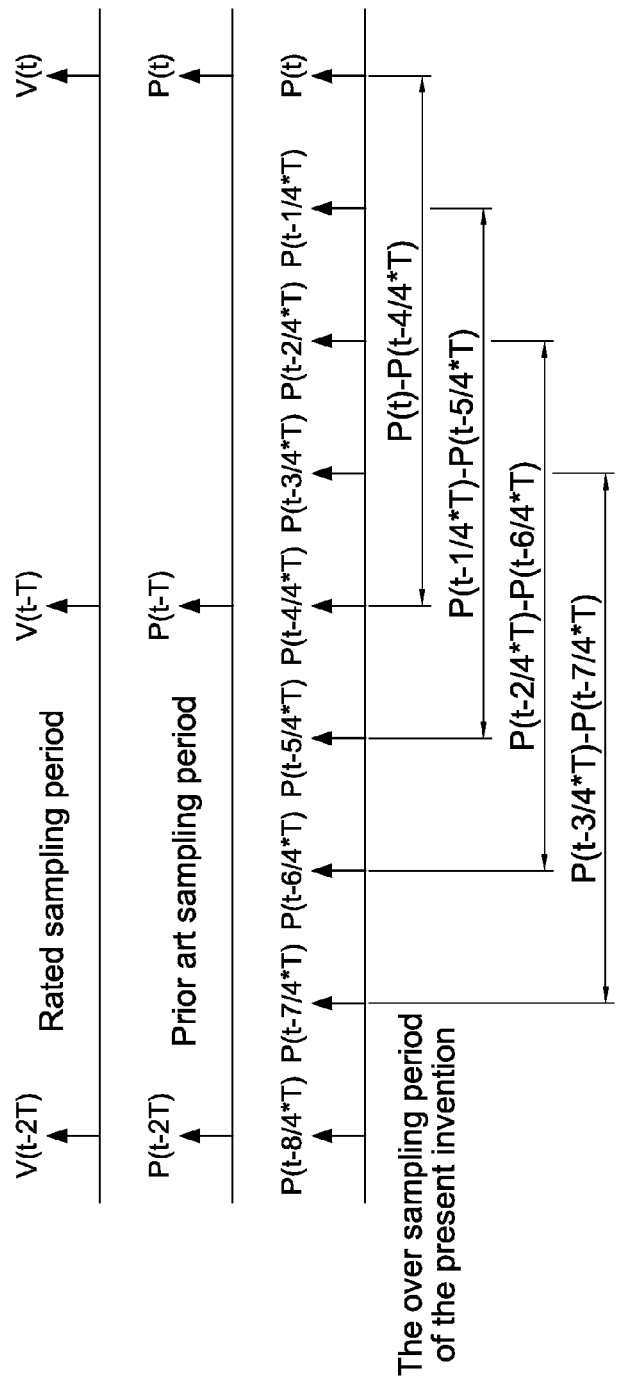
FIG. 5 shows the sampling scheme of the present invention.

The multiple-point smoothing method according to the present invention can be demonstrated by following example with over sampling factor M=4. The over sampling scheme is depicted in FIG. 5. The four sets of displacement differences are averaged and then divided by period T to obtain an initial speed estimation V(t). Therefore, the initial speed estimation V(t) has following expression:

$$V(t) = \left( \frac{P(t) - P\left(t - \frac{4}{4}T\right)}{T} + \frac{P\left(t - \frac{1}{4}T\right) - P\left(t - \frac{5}{4}T\right)}{T} + \frac{P\left(t - \frac{2}{4}T\right) - P\left(t - \frac{6}{4}T\right)}{T} + \frac{P\left(t - \frac{3}{4}T\right) - P\left(t - \frac{7}{4}T\right)}{T} \right) / 4$$

When the over sampling rate is M times of the rated sampling frequency, the general expression is:

$$V(t) = \frac{\sum_{k=0}^{M-1} P\left(t - \frac{k}{M}\right) - P\left(t - \frac{k+M}{M}T\right)}{MT}$$

The initial speed estimation V(t) calculated by the displacement average unit 26 is processed by a low pass filer to obtain a final speed estimation, which can be used for close loop control of motor.

Figure 6:
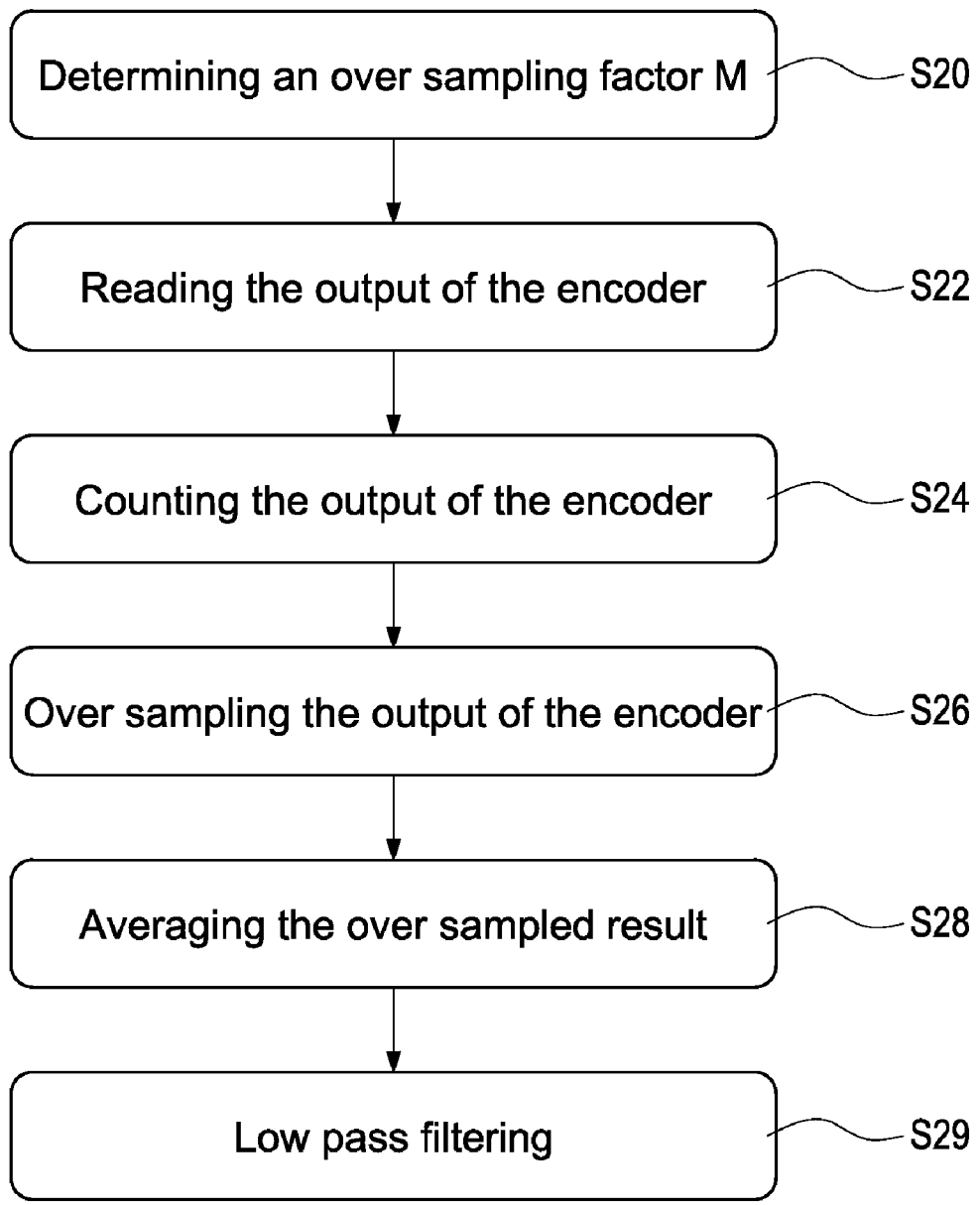
FIG. 6 shows the flowchart of the multiple-point smoothing method according to the present invention.

FIG. 6 shows the flowchart of the multiple-point smoothing method according to the present invention. An over sampling factor M is chosen (step S20) and then the output of an encoder is read (step S22) and counted (step S24). The position information output from the encoder is over-sampled (step S26). The over-sampled results are averaged (step S28) to obtain an initial speed estimation. The initial speed estimation is low pass filtered (step S29) to obtain a final speed estimation, which can be used for close loop control of motor.

The multiple-point smoothing method according to the present invention does not have the problem of phase delay in comparison with the prior art method (US pre-grant publication 20070043528 A1), especially when M is large. Moreover, the multiple-point smoothing method according to the present invention uses over sampling factor M of constant value, which is not changed with rotation speed. On the contrast, the prior art method (US pre-grant publication 20070043528 A1) uses moving average with window size based on the rotation speed of motor. Therefore, the prior art method cannot be used for high-speed servo control.

Figure 7:
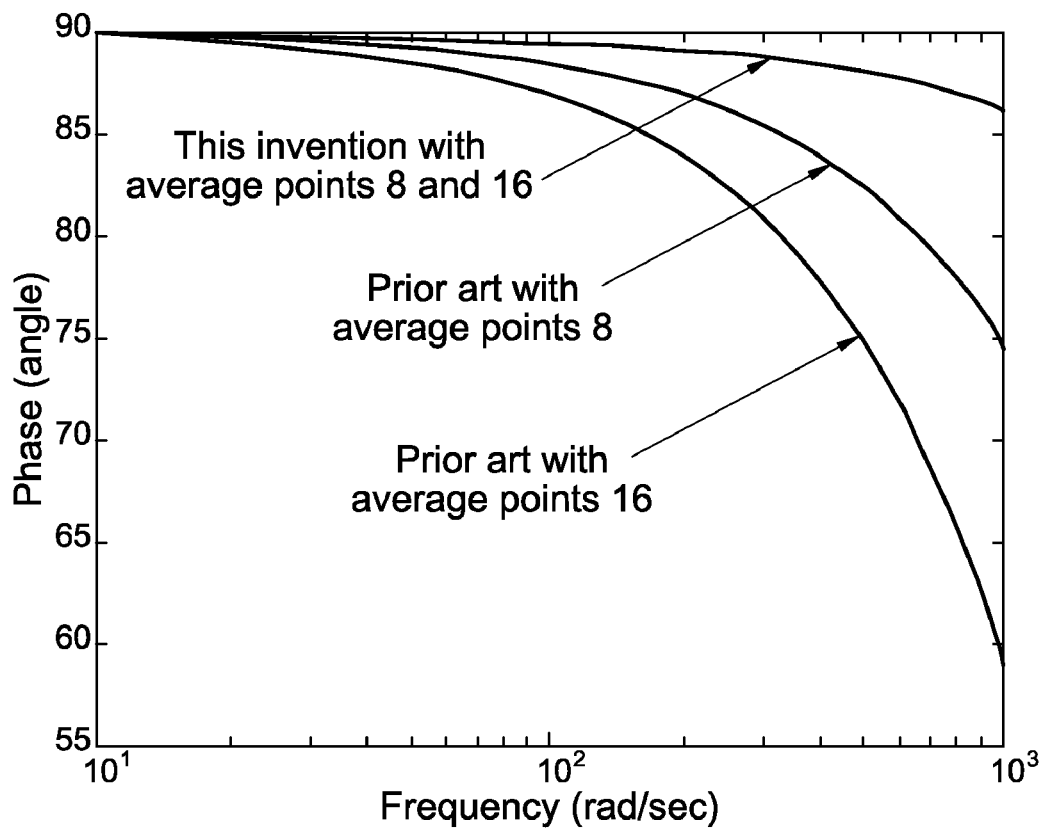
FIG. 7 shows the phase response for the method of the present invention and the prior art method.

FIG. 7 shows the phase response for the method of the present invention and the prior art method (US pre-grant publication 20070043528 A1) for over sampling factors M (which are average points in US pre-grant publication 20070043528 A1) of 8 and 16, respectively. As can be seen from this figure, the multiple-point smoothing method of the present invention does not induce time delay for signal when the over sampling factors M (average points) are increased to enhance smoothness of speed measurement. The inventor also finds that the smoothness of speed measurement is better when the over sampling factors M are increased. The ripples originally occur at rotation speed of $(60 \times fs/N_r)$ rpm for prior art measurement method. In the multiple-point smoothing method of the present invention, the ripples occur at rotation speed of $(60 \times fs \times M/N_r)$ rpm, which is M time better than the prior art measurement method. When M is selected to be large enough, the rotation speed influenced by ripples (hereinafter, the ripple speeds) is far larger than the actual rotation speed of motor. Therefore, the ripple problem can be overcome by the multiple-point smoothing method of the present invention when ripple speeds are larger than the actual rotation speed of motor.

Figure 8A:
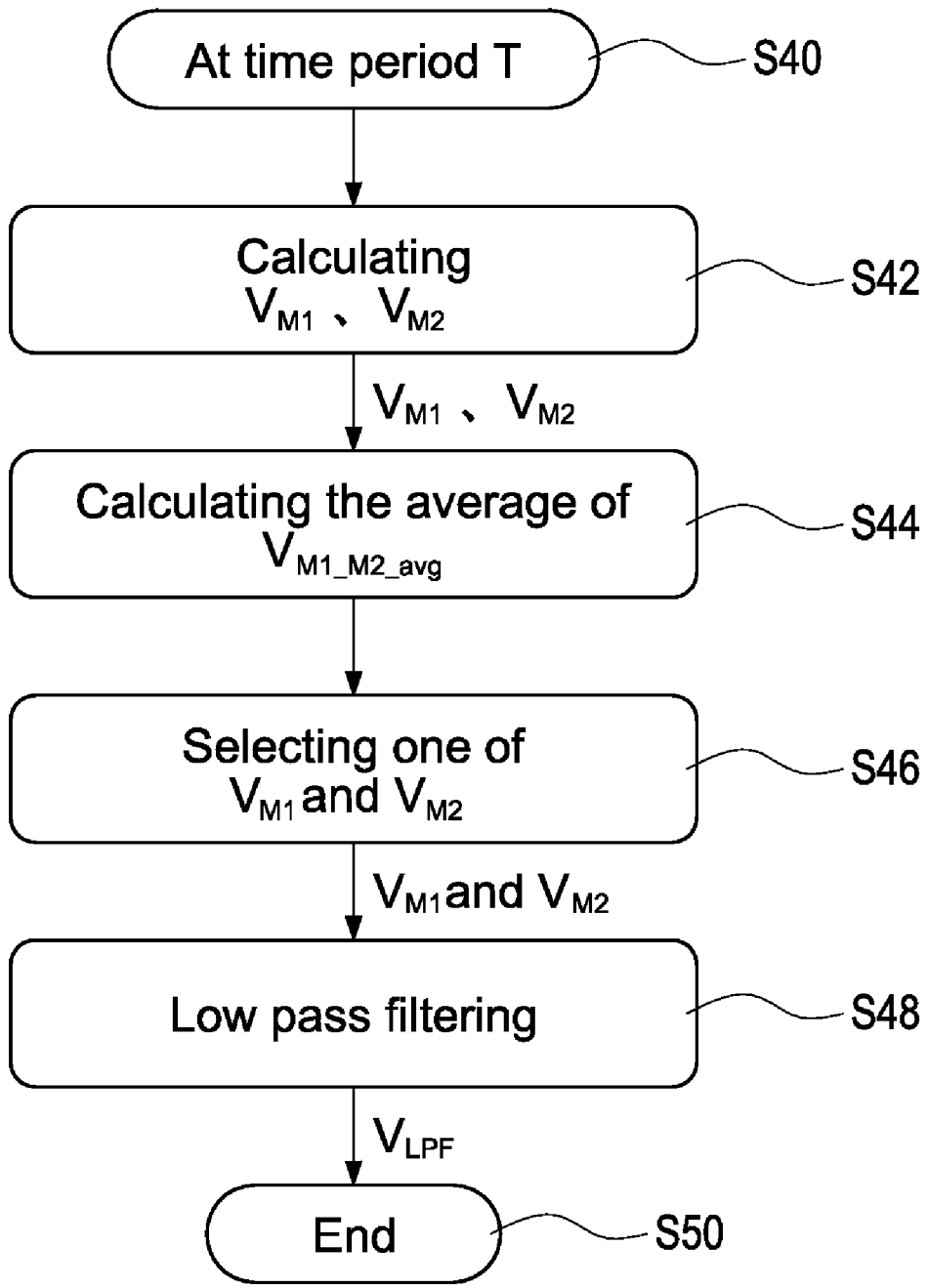
FIGS. 8A to 8C show the flowchart of a multiple-point smoothing method according to the second preferred embodiment of the present invention.
Figure 8B:
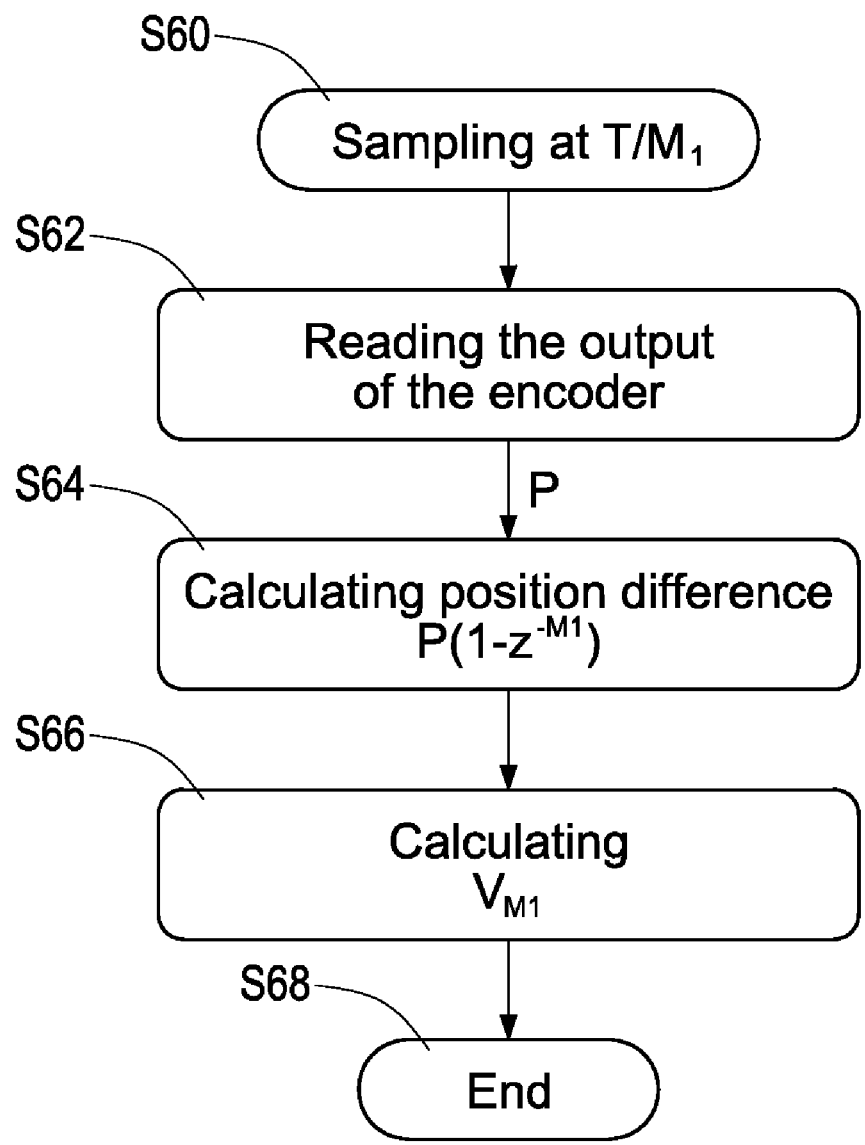
Figure 8C:
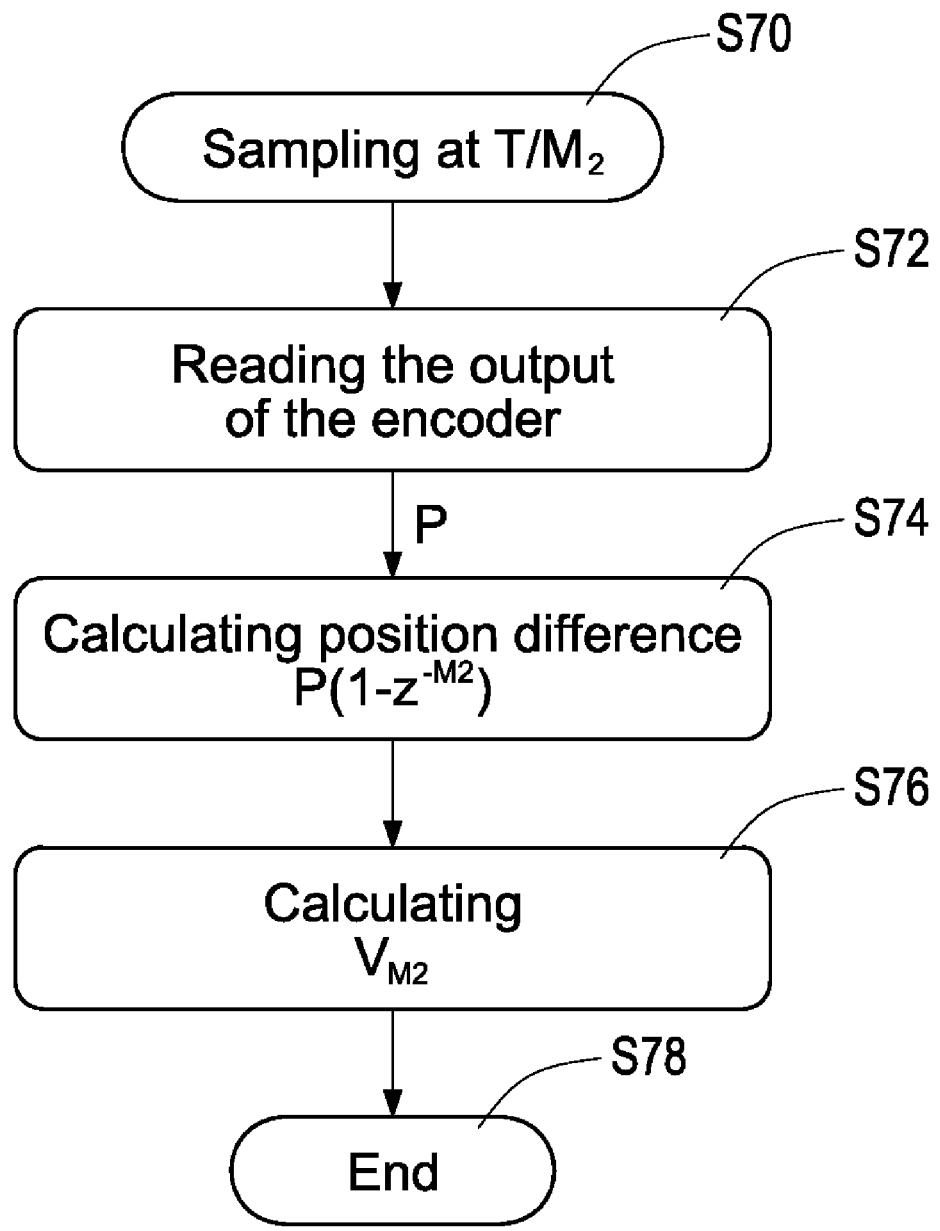

FIGS. 8A to 8C show the flowchart of a multiple-point smoothing method according to the second preferred embodiment of the present invention. The method in this preferred embodiment is intended to overcome the ripple in speed measurement occurring at ripple speeds $f_r = (M/N_r) \times 60 \times fs$ rpm. In this shown method, two over sampling factors M1 and M2 are selected to obtain two estimations $V_{M1}$ and $V_{M2}$, wherein $M_1 \neq M_2$. The ripples will occur at $f_r \times$(the least common multiple of $M_1$ and $M_2$). For example, the ripple speed fr is multiple of 36 rpm when the sampling time is $(6 \text{ kHz})^{-1}$, and the resolution of the encoder is 10000 pulses/turn.

The multiple-point smoothing method according to the second preferred embodiment of the present invention is referred to as a composite multiple-point smoothing method for motor-speed estimation and an example with $M_1=8$ and $M_2=9$ is as following:

$$\begin{cases} V_{M1} = \frac{P(1-z^{-8})(1+z^{-1}+z^{-2}+\ldots+z^{-(8-1)})}{8 \cdot T}, & (1) \\ z^{-1} \text{ indicates } \frac{T}{8} \text{ delay} \\ V_{M2} = \frac{P(1-z^{-9})(1+z^{-1}+z^{-2}+\ldots+z^{-(9-1)})}{9 \cdot T}, \\ z^{-1} \text{ indicates } \frac{T}{9} \text{ delay} \\ V_{M1\_M2\_avg} = \frac{(V_{M1}+V_{M2})}{2} \\ V = \begin{cases} V_{M2}, & \text{if } f_r \times (8N-1) < \quad N = \text{integer} \\ & V_{M1\_M2\_avg} < \\ & f_r \times \left(8N + \frac{1}{2}\right), \\ V_{M1}, & \text{else} \end{cases} & (2) \end{cases}$$

wherein $V_{M1}$ and $V_{M2}$ represent the initial speed estimation for $M_1=8$ and $M_2=9$, and $V_{M1\_M2\_avg}$ represents the average of the $V_{M1}$ and $V_{M2}$, the initial speed estimation for the composite multiple-point smoothing method uses the initial speed estimation $V_{M2}$ for $M_2$=9, when $$f_r \times (8N-1) < V_{M1\_M2\_avg} < f_r \times \left(8N + \frac{1}{2}\right),$$

where N is an integer.

The initial speed estimation for the composite multiple-point smoothing method uses the initial speed estimation $V_{M1}$ for $M_1$=8 when $V_{M1\_M2\_avg}$ is not in above range.

With reference now to FIGS. 8A to 8C, the sampling time is divided into $M_1$ and $M_2$ equal parts, respectively (step S40). The position output P from the encoder is sampled at interrupt time $$\frac{T}{M_1} \text{ and } \frac{T}{M_2}$$

and the position difference $P(1-z^{-M1})$ and $P(1-z^{-M2})$ are calculated. With reference also to the flowchart in FIGS. 8B and 8C, the initial speed estimations $V_{M1}$ and $V_{M2}$ for $M_1$ and $M_2$ are calculated (step S42). The average $V_{M1\_M2\_avg}$ of the $V_{M1}$ and $V_{M2}$ is calculated (step S44). One of the $V_{M1}$ and $V_{M2}$ is selected according to the formula (2) in step S46. The selected initial speed estimations $V_{M1}$ or $V_{M2}$ is low pass filtered (step S48) to obtain a final speed estimation $V_{LPF}$. The final speed estimation $V_{LPF}$ can be used for close-loop speed control.

According to simulation of the inventor, the speed estimation has ripple at speed of 36×8=288 rpm when M=8 and the speed estimation has ripple at speed of 36×9=324 rpm when M=9 if the method of the first preferred embodiment is used. The ripples at the two groups of speeds disappear when the composite multiple-point smoothing method according to the second preferred embodiment is used.

The advantage of the composite multiple-point smoothing method according to the second preferred embodiment can be explained by the example below. Provided that the ripple speed fr is 36 rpm and the method of the first preferred embodiment is used for estimating the speed of a motor system with maximum speed of 3000 rpm, the over sampling factor M needs to exceed 84 (84×36>3000). However, according to the composite multiple-point smoothing method of the second preferred embodiment, two sampling factors M=9 and M=10 are used and the least common multiple of 9 and 10 is 90, namely 90×36>3000. Therefore, two sampling factors prime to each other can be used as the sampling factors in the composite multiple-point smoothing method of the second preferred embodiment. The ripple problem in speed estimation can be overcome even the motor is operated in high speed.

The advantages of the present invention can be summarized as following:

The method of the present invention adopts an over-sampling scheme and the sampling frequency is higher than a rated sampling frequency for an encoder. Therefore, the method of the present invention generates smooth speed estimation even when the motor is operated in high speed.

Although the present invention has been described with reference to the preferred embodiment thereof, it will be understood that the invention is not limited to the details thereof. Various substitutions and modifications have suggested in the foregoing description, and other will occur to those of ordinary skill in the art. Therefore, all such substitutions and modifications are intended to be embraced within the scope of the invention as defined in the appended claims.

What is claimed is:

1. A multiple-point smoothing method for motor speed estimation, the method determining a speed estimation for a motor according to an output of an encoder and sending the speed estimation to a motor controller, the method comprising:
    determining an over sampling factor M which is an integer larger than one;
    reading the output of the encoder;
    counting the output of the encoder;
    performing an over sampling to the output of the encoder according to the over sampling factor M and a rated sampling frequency fs; and
    averaging the over sampled result to obtain an initial speed estimation.

2. The multiple-point smoothing method for motor speed estimation as in claim 1, further comprising:
    low-pass filtering the initial speed estimation to obtain a final speed estimation.

3. A multiple-point smoothing method for motor speed estimation, the method determining a speed estimation for a motor according to an output of an encoder and sending the speed estimation to a motor controller, the method comprising:
    determining a first over sampling factor M1 and a second over sampling factor M2;
    reading the output of the encoder;
    counting the output of the encoder;
    obtaining a first initial speed estimation V1, wherein the output of the encoder is over-sampled according to the first over sampling factor M1 and a rated sampling frequency fs, and the over-sampled output of the encoder is averaged to obtain the first initial speed estimation V1;
    obtaining a second initial speed estimation V2, wherein the output of the encoder is over-sampled according to the second over sampling factor M2 and the rated sampling frequency fs, and the over-sampled output of the encoder is averaged to obtain the second initial speed estimation V2;
    calculating an averaged speed estimation $V_{avg}$ by averaging the first initial speed estimation V1 and the second initial speed estimation V2; and
    selecting one of the first initial speed estimation V1 and the second initial speed estimation V2 as an initial speed estimation according to the averaged speed estimation $V_{avg}$.

4. The multiple-point smoothing method for motor speed estimation as in claim 3, wherein the step of selecting one of the first initial speed estimation V1 and the second initial speed estimation V2 is performed according to following formula:

$$\text{if } f_r \times (8N-1) < V_{avg} < f_r \times \left(8N + \frac{1}{2}\right),$$

where N is an integer,
    then using the second initial speed estimation V2 as the initial speed estimation;
    else using the first initial speed estimation V1 as the initial speed estimation;

wherein fr is a ripple speed and is expressed as $f_r=(60 \times f_s/N_t)$ rpm, wherein $N_t$ is pulse number generated by the encoder for one revolution.

5. The multiple-point smoothing method for motor speed estimation as in claim 3, wherein M1 and M2 are integer numbers prime to each other.

6. The multiple-point smoothing method for motor speed estimation as in claim 3, further comprising:

low-pass filtering the initial speed estimation to obtain a final speed estimation.

7. The multiple-point smoothing method for motor speed estimation as in claim 3, wherein the over sampling factors M1 and M2 are integers larger then one.

* * * * *